United States Patent [19]
Silver et al.

[11] Patent Number: 5,230,695
[45] Date of Patent: Jul. 27, 1993

[54] KNEE BRACE SUSPENSION SYSTEM INCLUDING NON-SLIPPAGE INFLATABLE AIR PILLOWS

[76] Inventors: Daniel M. Silver, 231 N. Rockingham Ave., Los Angeles, Calif. 90049; Richard Nauert, 861 Production Pl., Newport Beach, Calif. 92663; Russell A. Rothenberg, 4267 Marina City Dr., Ste. 1014, West Tower South, Marina del Rey, Calif. 90292

[21] Appl. No.: 911,738
[22] Filed: Jul. 10, 1992
[51] Int. Cl.⁵ ............................... A61F 5/00
[52] U.S. Cl. ..................... 602/13; 602/26; 602/16
[58] Field of Search ............ 602/5, 13, 16, 23, 26

[56] References Cited

U.S. PATENT DOCUMENTS

| | | | |
|---|---|---|---|
| 891,181 | 6/1908 | Mitchell | 602/13 |
| 3,581,741 | 6/1971 | Rosman | 602/26 X |
| 3,868,952 | 3/1975 | Hatton | 602/13 |
| 4,157,713 | 6/1979 | Clarey | 602/13 |
| 4,182,320 | 1/1980 | Sweeney | 602/13 |
| 4,657,003 | 4/1987 | Wirtz | 602/13 |
| 4,699,130 | 10/1987 | Hossler | 602/13 |
| 4,872,448 | 10/1989 | Johnson, Jr. | |
| 4,966,133 | 10/1990 | Kausek | |
| 4,982,264 | 1/1991 | Miller | |
| 5,107,823 | 4/1992 | Fratesi | 602/26 X |

Primary Examiner—Richard J. Apley
Assistant Examiner—Linda C. M. Dvorak
Attorney, Agent, or Firm—Keith D. Beecher

[57] ABSTRACT

An orthopedic knee brace which includes a thigh cuff and which also includes a pair of inflatable air pillows interposed between the thigh cuff and the thigh of the wearer to prevent slippage. The air pillows are mounted on the cuff to be located on the opposite sides of the femur of the wearer within the medial femoral hollows in position to engage the femoral condyles. A unique miniature pump is also provided for inflating the air pillows.

7 Claims, 2 Drawing Sheets

KNEE BRACE SUSPENSION SYSTEM INCLUDING NON-SLIPPAGE INFLATABLE AIR PILLOWS

BACKGROUND OF THE INVENTION

The invention relates generally to an orthopedic device of the type disclosed in Co-Pending application Ser. No. 07/845,650 filed Mar. 4, 1992 and assigned to the present assignee. The orthopedic devices of the present invention and of the co-pending application are in the form of knee braces for controlling ligament instability, each of the braces having upper and lower cuffs joined together by specially designed polycentric hinges of the type described, for example, in Co-Pending application (K-3538).

A typical orthopedic knee brace of the type with which the present invention is concerned is described, for example, in U.S. Pat. No. 4,966,133 - Kausek. As pointed out in that patent, when the ligament surrounding the knee has been traumatized by injury or by surgery, a supporting brace is commonly used to provide stability to the knee while still permitting movement of the knee. The brace must provide stability when forces are applied to the knee in the medial and lateral (side) planes, and in the anterior (front) and posterior (rear) planes. In addition, the brace must provide rotational stability to prevent excessive axial rotation of the tibia with respect to the femur. The brace must also prevent forward movement of the tibia with respect to the femur, a function provided in the normal knee by the anterior cruciate ligament.

As pointed out in Co-Pending application Ser. No. 07/845,650, a problem encountered in the prior art knee braces is the tendency, particularly for the upper cuff which surrounds the side of the wearer, to slip down along the thigh. The cuffs are normally held in place by straps with VELCRO fasteners, and in view of the slippage tendency, it is often difficult to adjust the straps for optimum effect and comfort, without the tendency for the upper cuff to slip down due to muscle action.

The brace disclosed in the Co-Pending application Ser. No. 07/845,650 includes a simple means which is easily adjustable to assure that the side cuff may be mounted for optimum effect and comfort and still be held firmly in place without excessive slippage despite muscle action of the wearer. The foregoing is achieved in the brace of the Co-Pending application by mounting one or more air pillows between the side of the wearer and the cuff, and by providing a miniature pump coupled to the air pillows. The pump permits the wearer to pump the air pillows to a desired inflated condition to hold the cuff firmly in place, without affecting the comfort of the wearer.

The brace of the present invention is of the same general type as the brace disclosed in the Co-Pending application Ser. No. 07/845,650. However, the brace of the present invention is more effective in preventing slippage in that it includes a pair of air pillows which are mounted on the internal surface of the upper cuff in positions to be located on the opposite sides of the femur of the wearer within the medial and lateral femur hollows and engaging the condyles (knuckles) of the femur. Accordingly, when the air pillows are inflated, the condyles act in a positive manner to prevent any slippage of the upper cuff downwardly, and cause the upper cuff to be held firmly in place.

DETAILED DESCRIPTION OF THE ILLUSTRATED EMBODIMENT

Figure 1:
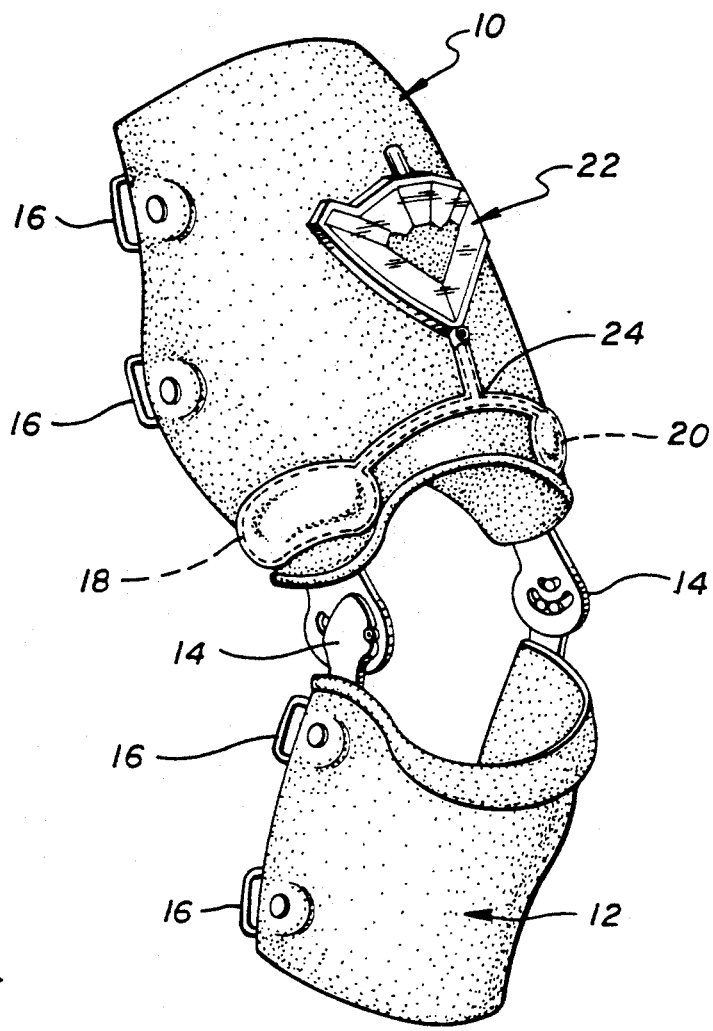
FIG. 1 is a perspective representation of the upper and lower cuffs and interconnecting hinges of a knee brace constructed to incorporate the concepts of the present invention.

As stated above, FIG. 1 is a perspective representation of a portion of an orthopedic knee brace which includes an upper cuff 10 which engages the thigh of the wearer, and a lower cuff 12 which engages the leg of the wearer below the knee. The upper and lower cuffs 10 and 12 are hinged to one another by appropriate hinges 14. The upper and lower cuffs are formed, for example, of a Kevlar/fiberglass composition, or any other appropriate material. The cuffs are conventionally held in place by straps connected to the cuffs through fastener brackets 16, with the straps surrounding the side and leg of the wearer, and being held in place by appropriate fasteners such as VELCRO fasteners.

Figure 2:
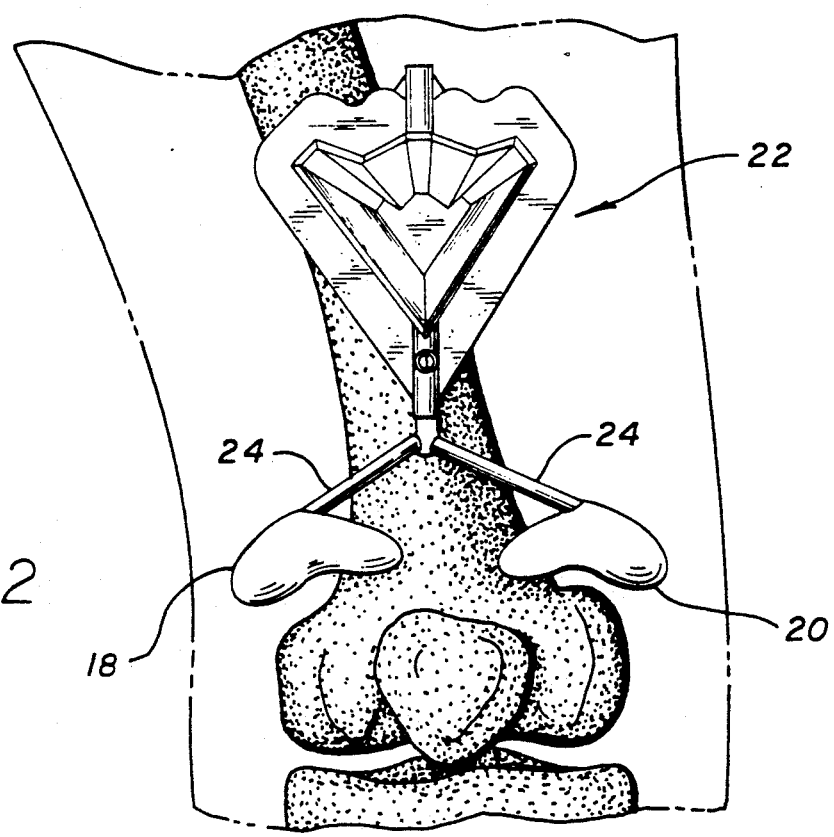
FIG. 2 is a schematic representation showing the location of a pair of air pillows mounted on the internal surface of the upper cuff of the knee brace of FIG. 1, and showing the manner in which the air pillows engage the condyles of the femur of the wearer to hold the upper cuff firmly in place.

In accordance with the invention, a pair of air pillows 18 and 20 are interposed between the upper cuff 10 and the side of the wearer. The air pillows are positioned, as shown in FIG. 2 to be located on opposite sides of the femur of the wearer within the lateral and medial femoral hollows in the distal femoral metaphysis area of the femur. The air pillows 18 and 20 engage the femoral condyles (knuckles) so that when the air pillows are inflated, they firmly hold the upper brace 10 from slipping, since any downward slippage is prevented by the engagement of the air pillows with the condyles.

Figure 4:
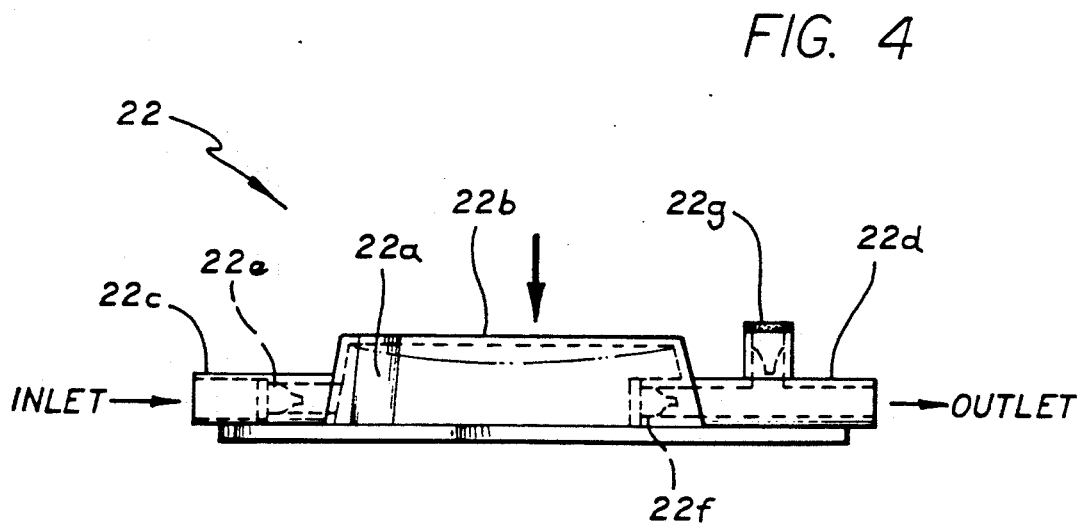
FIG. 4 is a side elevation of the pump of FIG. 3.
Figure 3:
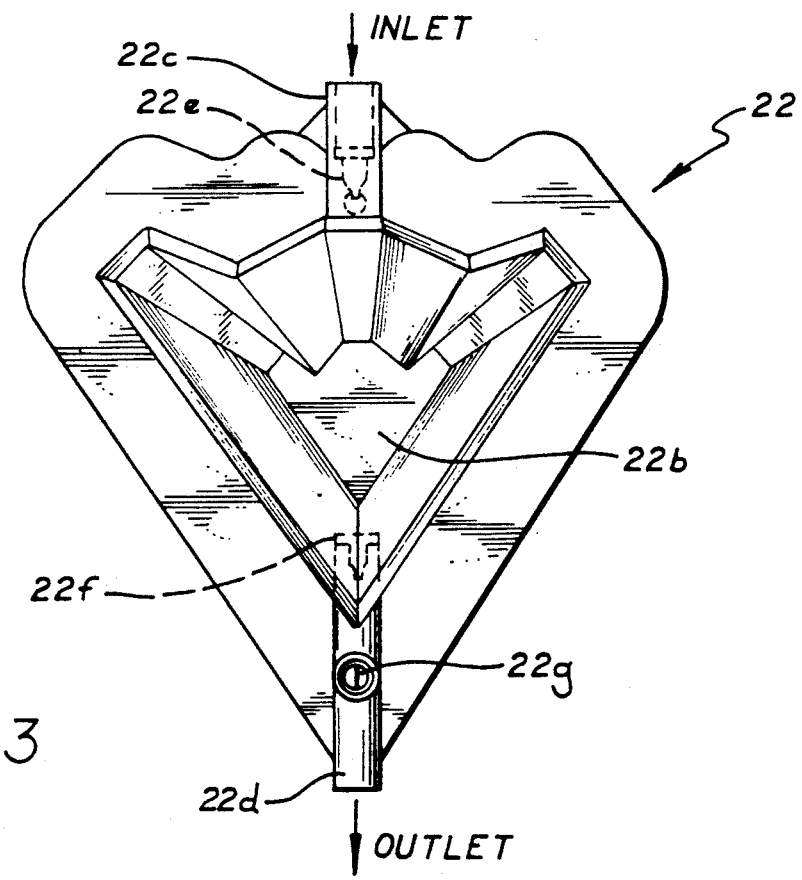
FIG. 3 is a top plan view of a pump which is mounted on the upper cuff of the knee brace of FIG. 1 for inflating the air pillows.

The air pillows 18 and 20 may be inflated by a miniature air pump 22 which is shown in detail in FIGS. 3 and 4. The air pump 22 permits the wearer, by repeatedly depressing and releasing the resilient top of the pump, to introduce pressurized air into the air pillows through a tube 24.

It will be appreciated that the knee brace shown in FIG. 1 may be easily mounted on the leg of the wearer, with the upper and lower cuff 10 and 12 being held in place by appropriate straps (not shown). Then, the pump 22 is operated to inflate the air pillows 18 and 20, thereby to cause the air pillows to hold the upper cuffs 10, and other components, from slipping down the thigh of the wearer. The inflated air pillows firmly and positively hold the upper cuff and associated components in place around the thigh of the wearer, because of their engagement with the condyles of the femur, thereby preventing any slippage of the upper cuff, this being achieved without detracting in any way from the comfort of the device.

The miniature pump 22, as shown in FIGS. 3 and 4, may be formed of an integral resilient plastic material to define a housing 22a having a resilient top 22b. The pump has a generally triangular configuration, as shown in FIG. 1, with an inlet 22c being formed at one end, and an outlet 22d being formed at the other end. A resilient "duck bill" valve 22e is inserted into the inlet, and a second resilient "duck bill" valve 22f is inserted into the outlet. The duck bill valves are positioned so that when the resilient top 22b is depressed, any air within the housing 22a is expelled into the air bladders 18 and 20 at relatively high pressure through the outlet 22d. Then, when the resilient top is released, air is drawn into the housing 22a through the inlet 22c. Accordingly, repeated operation of the resilient top 22b causes pressurized air to be pumped into the air pillows 18 and 20.

A further "duck bill" valve 22g is mounted in the outlet 22d, and it may be manually distorted to cause air within the air pillows 18 and 20 to be exhausted to the atmosphere.

The invention provides, therefore, a simple and economical knee brace in which the upper cuff is controlled by appropriately positioned air pillows so as to assure that there will be no downward slippage of the cuff along the thigh of the wearer.

It will be appreciated that while a particular embodiment of the invention has been shown and described, modifications may be made. It is intended in the claims to cover all modifications which come within the true spirit and scope of the invention.

We claim:

1. An orthopedic knee brace including: an upper cuff configured to be draped around the thigh of the wearer; a pair of air pillows positioned between the cuff and the thigh of the wearer and located to be disposed on opposite sides of the femur of the wearer and having a size to be positioned solely within the medical and lateral femoral hollows and engaging the upper region of the femoral condyles; and means coupled to the air pillows for introducing pressurized fluid into the interior of the air pillows to inflate the air pillows and cause them to prevent downward slippage of the cuff.

2. The orthopedic knee brace defined in claim 1, in which air pillows are mounted on the internal surface of the cuff.

3. The orthopedic knee brace defined in claim 1, in which said means for introducing pressurized fluid into the interior of said air pillows comprises a miniature pump mounted on said upper cuff and coupled to said air pillows.

4. The orthopedic knee brace defined in claim 3, in which said miniature pump comprises a housing having an inlet at one end and an outlet at the other end and having resilient top serving as an inflater, two one-way valves respectively mounted in the inlet and outlet of said housing so that depression of said top forces pressurized fluid into said air pillows and release of said top draws pressurized fluid into said housing.

5. The orthopedic knee brace defined in claim 4, in which said one-way valves are formed of resilient material and are duck bill valves.

6. The orthopedic knee brace defined in claim 3, in which includes a third manually operable exhaust valve mounted in said outlet for exhausting the pressurized fluid from the air pillows.

7. The orthopedic knee brace defined in claim 6, in which said third valve is formed of resilient material and is a duck bill valve.

* * * * *